United States Patent

Vadgama et al.

[11] Patent Number: 5,567,290
[45] Date of Patent: Oct. 22, 1996

[54] SENSOR DEVICES

[75] Inventors: Pankaj M. Vadgama, Manchester; Ian M. Christie, Stockport; Yazid M. Benmakroha, Manchester; Subrayal M. Reddy, Preston, all of United Kingdom

[73] Assignee: The Victoria University of Manchester, Manchester, England

[21] Appl. No.: 374,740

[22] PCT Filed: Jul. 23, 1993

[86] PCT No.: PCT/GB93/01566

§ 371 Date: Mar. 10, 1995

§ 102(e) Date: Mar. 10, 1995

[87] PCT Pub. No.: WO94/02585

PCT Pub. Date: Feb. 3, 1994

[30] Foreign Application Priority Data

Jul. 28, 1992 [GB] United Kingdom ............... 9215973

[51] Int. Cl.$^6$ ..................................................... G01N 27/26
[52] U.S. Cl. .......................... 204/415; 204/403; 435/817; 435/287.1; 435/287.9; 435/288.7
[58] Field of Search ................................ 204/403, 415, 204/418; 435/817, 288, 291

[56] References Cited

U.S. PATENT DOCUMENTS

| 4,076,656 | 2/1978 | White et al. ...................... 260/2.5 M |
| 4,557,955 | 12/1985 | Walch et al. ...................... 428/35 |
| 5,312,590 | 5/1994 | Gunasingham ...................... 204/403 |
| 5,326,449 | 7/1994 | Cunningham ...................... 204/403 |
| 5,356,786 | 10/1994 | Heller et al. ...................... 204/403 |

FOREIGN PATENT DOCUMENTS

| 216577 | 4/1987 | European Pat. Off. . |
| 503943 | 9/1992 | European Pat. Off. . |

*Primary Examiner*—Bruce F. Bell
*Attorney, Agent, or Firm*—Cushman Darby & Cushman

[57] ABSTRACT

Sensor devices for examining fluid samples having, between the sample under examination and a detector, a membrane made of polyvinyl chloride in un-plasticized form. This membrane material acts as a barrier to paracetamol and sugars but is permeable to hydrogen peroxide and to oxalate, so these species can be determined after passing through the membrane. When they are not present as such in the sample, they may be formed from analytes which are sought (e.g. by enzymic action, which is especially applicable to the determination of glucose, using an oxidase enzyme). The membranes may be made by solvent casting, conveniently to a thickness of 10 to 40 μm, and used in electrolytic systems with a platinum anode. The membrane material can be formed into multi-layer membranes, which may incorporate layers of material to protect it or modify the permeability, or added materials for example enzymes.

24 Claims, No Drawings

SENSOR DEVICES

This invention relates to sensor devices such as are used in the determination of a component or components which may be present in a fluid sample, such as a physiological fluid (e.g. blood) or other fluids of biological origin (e.g. fruit), process fluids or effluents.

Many forms of sensor have been proposed, and commonly these rely on some form of membrane to control the extent to which the components present in a sample under examination can gain access to an electrode, at which they can then be detected and determined. Especially, it is well known to make sensors using membranes to separate the media being analyzed from the active electrode itself. The main function of the membrane is to separate, as far as possible, those components which are desirable (i.e. can take part in the reactions at the electrode on which the desired determination depends) from interferents (i.e. compounds which may be present but are undesirable because they either interfere with the progress of the desired determination reactions or take part in reactions of their own which compete with those of the component sought and distort or overwhelm the signals which are to be measured. The forms of construction have much in common with each other, and mainly differ in the nature of the membrane or media within it or combined with it in some way.

Some forms of sensor rely on the components used to make the membrane, while others rely on the mode of fabrication of the membrane, selecting its physical properties (for example its porosity) or treatments given to it, as these factors can control its effectiveness and selectivity in use.

Other forms of sensors incorporate an enzyme, which converts one substrate compound or analyte into another which may then be more easily measured. Especially, it is known to use oxidase enzymes, which generate hydrogen peroxide—a substance which can be measured very conveniently and very accurately by electrolytic methods, especially amperometrically. An example is European Patent No. 216577 (of ICI PLC) which specifies an enzyme electrode sensor with membrane barrier of low (>5%) porosity.

Materials which have been proposed for the fabrication of membranes for sensors include polyvinyl chloride (PVC), but only in plasticized form, as described in European Patent Application No. 92302131.5, where the plasticizer performs a necessary part of the function of the membrane.

Such known sensors, utilising various membrane materials, are very valuable in analytical techniques and the analysis of biological fluids (e.g. blood) for the presence of substances considered critical for medical reasons—e.g. glucose and other materials which may be oxidizable or reducable, or have toxic properties.

We have now found that the selectivity of such a membrane-enclosed sensor can be significantly and surprisingly modified and improved by making the membrane of polyvinyl chloride (PVC) itself, in un-plasticized form.

Thus according to our invention we provide an improved sensor device comprising means for detecting components present in fluid samples and providing an output representative of the content of said component comprising a detecting means and a membrane barrier between the detecting means and the sample to be analyzed, characterised in that the membrane barrier is composed of polyvinyl chloride (PVC) itself, in un-plasticized form.

The detecting means is most conveniently of one of an electrochemical nature, but other types (e.g. spectrophotometric or optical detecting systems) may be used if desired. The detecting means will usually comprise an electrode system and a liquid or gel phase electrolyte-containing medium. In most applications the electrolyte will be aqueous (i.e. aqueous or aqueous-based) but the use of non-aqueous electrolyte media (for example organic-based media) is not excluded.

According to our invention we also provide a method for determining a component in a fluid sample, which comprises contacting the sample with a sensor device as defined above.

Especially, in the devices and method of our invention, the sensor device comprises a detecting means in contact with an electrolyte medium and both associated with a membrane of polyvinyl chloride (PVC) itself, in un-plasticized form, which provides an interface for contact with a sample to be analyzed and interposed between the active electrode (anode) of the cell used as detector. Alternative forms of construction may have both the electrodes of the detecting means (cell) enclosed within the PVC membrane (so that both are separated from the sample) or (b) only the anode of the detecting means (cell) enclosed within the PVC membrane (so that the PVC membrane is between the electrodes and the cathode is not separated from the sample). Of these, the former is very convenient and compact, but the latter is more simple and is made practicable by the fact that PVC in un-plasticized form is less insulating in its properties, and $H^+$ ions can pass through it.

The sensor device of our invention can have a single membrane or, if desired, multiple layers of membrane material. When multiple layers of membrane are used, these may be the same or different. The preference for the position to be occupied by the un-plasticized PVC membrane differs to some degree according to the particular use to which the sensor is being applied and what substrate compound is to be detected by the sensor.

The governing factor is mainly the fact that un-plasticized PVC is permeable to hydrogen peroxide and some low molecular weight species (for example oxalate) but impermeable to some sugars, and permeable to others for example glucose. Thus, when the sensor is to be used for detecting a species to which the PVC is impermeable, a sensor assembly is best made with an enzyme (with which the desired substrate can interact and generate a species which can pass through the un-plasticized PVC) situated outside the un-plasticized PVC membrane, so that the desired species in the sample under examination can make contact with the enzyme—either directly or indirectly, through another selective membrane layer—and thereby generate a species to which the un-plasticized PVC membrane is permeable. Especially, when glucose is the species sought, an oxidase enzyme can be used and the hydrogen peroxide thus generated can pass through the un-plasticized membrane and be determined at the detector means.

When multiple membrane layers are used, any membrane layer or layers other than any comprised of un-plasticized PVC may be made of any of the wide variety of materials known in the art. Examples of these include dialysis membranes, and in general are preferably non-diffusion limiting membranes, at least to the extent that they do not limit diffusion and passage of desired species towards the detecting means. When un-plasticized PVC is used as in inner membrane (i.e. a layer which is not the outermost), then one or more outer layers may be used which are of material which protects the sensor assembly in a mechanical manner (e.g. from mechanical damage) or in a chemical or any other manner considered appropriate for the use to which it is to be applied. Thus for example, there may be used an outer layer comprising a polycarbonate (especially in a porous form).

The active electrode may be any of those known in the art, for example a metal electrode, but especially a platinum anode. This is most conveniently made in combination with a silver/silver chloride counter electrode, as for example in the so-called Clark electrode, which comprises a platinum electrode surrounded by a silver/silver chloride ring.

The PVC (polyvinyl chloride) may, be any polymer of vinyl chloride, as for example those made and available commercially, but should be free from any added plasticizer (an ingredient which is often present in some commercial products intended for uses such as molding). Such "un-plasticized" PVC polymers are readily obtainable in commerce, however, and it is necessary only for the quality and purity of any polymer to be checked, whether by its specification or labelling. The molecular weight of the PVC is relatively non-critical, and most commercial grades will be satisfactory in use. A typical molecular weight is in the range 10,000 to 200,000, but others may be used if desired.

The material (i.e. the un-plasticized polyvinyl chloride) may be made into membranes by any conventional method. Most conveniently, this can be done by solution casting techniques, using solvents to dissolve the polymer and then spreading the solution on a plate or flat surface and allowing the solvent to evaporate. A convenient solvent is tetrahydrofuran (THF), but other solvents or mixtures of solvents which are known to be able to dissolve PVC be used if desired.

The thickness of the membranes can be of the order already used conventionally in the art, but my be varied as found most appropriate having regard for the particular mixed polymer composition being used and the conditions under which it is to be used. Thus a convenient thickness is in the range 10 to 40 μm, though larger or smaller thicknesses can be used if desired.

There are two principal forms of construction which may be used to secure the advantages of the new membrane material we now propose. In one, the un-plasticized PVC is the outer membrane, and in the other it is the inner membrane.

The forms using an enzyme will have basically the construction sequences:

| (A) | OR | (B) |
|---|---|---|
| Sample | | Sample |
| Membrane (e.g. Polycarbonate) | | Membrane (Un-plasticized PVC) |
| enzyme | | enzyme |
| Inner (Un-plasticized PVC) membrane | | Inner (e.g. polycarbonate) membrane |
| Electrode. | | Electrode. |

For these, the components (apart from the un-plasticized PVC membrane) are mainly the conventional ones, and the many variants known in the art may be used.

Un-plasticized PVC is not sufficiently permeable to glucose, so direct electrochemical detection of glucose cannot be achieved through this material as membrane. However, it is permeable to hydrogen peroxide, so enabling an alternative glucose-permeable membrane and an oxidase enzyme to be used to produce hydrogen peroxide, which then can selectively permeate the un-plasticized PVC membrane.

This un-plasticized PVC membrane has a particular advantage over plasticized PVC in that it is (unlike the plasticized form) impermeable to paracetamol—so that this compound is excluded from interfering with hydrogen peroxide detection, as well as ascorbate/urate. This selectivity against paracetamol and the like while in favor of hydrogen peroxide is a valuable property which is not easily found and it very useful in clinical and related analytical, diagnostic and monitoring work.

Consequently, any other sensor device or system using an oxidase enzyme to generate hydrogen peroxide can, with advantage, incorporate an un-plasticized PVC membrane as part of its construction, especially as an inner membrane near to the active electrode surface.

Another advantage is that sensor devices of the electrolytic (amperometric) type are often used for examination of biological fluids for example blood, urine, and the like. It happens that urine contains a number of interferents which—even though their identity has not yet been established—have the ability to permeate many of the known conventional membrane materials, for example plasticized PVC, and so interfere severely with the accurate estimation of components such as hydrogen peroxide and of compounds which can be used to generate it. The un-plasticized form of PVC does not allow these unidentified components to pass through, is it constitutes an effective barrier to them and facilitates the wider applicability and accuracy of measurement. Thus, for many applications the un-plasticized PVC membrane will be preferable, though it will not always be so in applications in which it is desired to have a phenolic compound permeating the membrane.

Another use for the un-plasticized PVC membrane is in the construction of a sensor device for the determination of oxalate. It acts in this in two ways, both of which are valuable. One is a form of sensor in which the un-plasticized PVC membrane is used as an inner membrane beneath a layer or membrane comprising an oxalate oxidase system, so that hydrogen peroxide is generated from the sample and the resulting hydrogen peroxide passes through the un-plasticized PVC membrane; this relies on its action as a membrane selectively permeable to hydrogen peroxide.

Alternatively, the un-plasticized PVC membrane can be used as an outer layer with the means for oxalate detection beneath it; this relies on its unexpected ability to act as a membrane selectively permeable to oxalate. Un-plasticized PVC is the only material that we know of at present which is oxalate-selective, and the mechanism by which it performs in this way is still not clear to us. In this mode or embodiment of our invention, the means for detecting the oxalate which has passed through the un-plasticized PVC membrane may be any of those known and may be either an enzyme one (oxalate oxidase based) or one which detects and measures the oxalate directly by electrolytic action. This may be amperometric, and the pH of the medium around the active electrode may be adjusted as may be found most appropriate by simple trial.

Whatever the mechanism by which the permeability to oxalate takes place, the ability of an un-plasticized PVC membrane to act so as to exclude serum and urine interferents from the active electrode region of a sensor is true and highly effective and a valuable feature of this invention.

An example of a basic construction sequence utilizing this un-plasticized PVC membrane can be represented as follows:

(1) SAMPLE
(2) ========== un-plasticized PVC membrane
(3) ENZYME (Oxidase)
(4) ========== inner membrane
(5) ELECTRODE.

In this, oxalate or oxalic acid from sample (1) passes through the un-plasticized PVC membrane (2) and then, by contact with the enzyme (3), generates hydrogen peroxide and carbon dioxide. The hydrogen peroxide then passes through the inner membrane (4) to the electrode (5), at which it is determined electrolytically.

The inner membrane (4) may be of any convenient material—for example a dialysis membrane or a polycarbonate membrane—intended to perform such actions as regulation of the flow of components to electrode (5) (should this be considered desirable) or to provide mechanical protection and add to the robustness of the sensor assembly and minimize risk of damage to the innermost electrode elements.

Thus according to our invention we also provide, as useful new products, membranes comprising un-plasticized polyvinyl chloride. Especially, we provide these in the form of multi-layer membrane products, in which at least one layer is formed of un-plasticized polyvinyl chloride and is combined with one or more layers of other materials of appropriate properties to enhance the properties of the un-plasticized polyvinyl chloride itself. Such materials may be of appropriate permeability to regulate the access of components before or after passage through the un-plasticized polyvinyl chloride, and/or of a physical form or strength which protects the un-plasticized polyvinyl chloride from damage or provides it with any desired degree of stability of shape or positioning in use.

Especially, we provide membranes of un-plasticized polyvinyl chloride incorporating an enzyme, for example an oxidase. In these, the enzyme may be immobilized by the chemical means known in the art, or they may be held between the layers of a multi-layer structure.

We claim:

1. A sensor device comprising means for detecting components present in fluid samples and providing an output representative of the content of said component, comprising a detecting means and a membrane barrier between the detecting means and the sample to be analyzed, characterized in that the membrane barrier is composed of polyvinyl chloride (PVC) itself, in un-plasticized form and being selectively permeable to hydrogen peroxide, oxalate and oxalic acid and impermeable to paracetamol.

2. A sensor device as claimed in claim 1 wherein the detecting means comprises an electrolytic sensor.

3. A sensor device as claimed in claim 1 or claim 2 which comprises a detecting means in contact with an electrolyte medium which is in contact with a membrane of polyvinyl chloride (PVC) itself, in un-plasticized form, which provides an interface for contact with a sample to be analyzed and interposed between the active electrode of the cell used as detector.

4. A sensor device as claimed in claim 3 wherein the electrolyte medium is contained in a liquid or gel phase.

5. A sensor device as claimed in claim 3 wherein an enzyme is placed between the sample to be analyzed and the membrane to convert a component or analyte to be determined in the sample into another compound which passes through the membrane and is then detected and measured by the detecting means.

6. A sensor device as claimed in claim 5 for detecting a species to which un-plasticized polyvinyl chloride is impermeable, wherein the enzyme is located between the un-plasticized polyvinyl chloride membrane and sample to be analyzed, so that the desired species in the sample under examination first contacts the enzyme and reacts to generate a species which passes through the un-plasticized polyvinyl chloride membrane to the detecting means.

7. A sensor device as claimed in claim 6 wherein the enzyme is an oxidase, which is used to interact with an oxidizable component to generate hydrogen peroxide—to which un-plasticized polyvinyl chloride is permeable.

8. A sensor device as claimed in claim 5 for detecting a species to which the un-plasticized polyvinyl chloride is permeable, wherein the enzyme is located within the un-plasticized polyvinyl chloride membrane, so that the desired species in the sample under examination first passes through the un-plasticized polyvinyl chloride membrane and then makes contact with the enzyme and reacts to generate a species to which the detecting means is responsive.

9. A sensor device as claimed in claim 1 or claim 2 comprising (1) a detecting means, (2) a membrane of un-plasticized PVC and (3) an electrolyte medium positioned between and in contact with (1) and (2), and with membrane (2) forming an interface with a sample to be analyzed.

10. A sensor device according to claim 9 wherein the detecting means is an active electrode.

11. A sensor device according to claim 10 wherein the active electrode is an anode.

12. A sensor device as claimed in claim 9 wherein the electrolyte medium is contained in an aqueous-based liquid or gel phase.

13. A sensor device as claimed in claim 1, wherein the polyvinyl chloride has a molecular weight in the range 10,000 to 200,000.

14. A sensor device as claimed in claim 1, wherein the polyvinyl chloride membrane has a thickness in the range 10 to 40 μm.

15. A sensor device as claimed in claim 1, wherein the polyvinyl chloride membrane is made by solution casting.

16. A sensor device as claimed in claim 1, wherein the active electrode of the detecting means is made of platinum.

17. A sensor device as claimed in claim 1, wherein the membrane of un-plasticized polyvinyl chloride is used as an inner membrane in conjunction with one or more outer layers of material which protects the sensor assembly.

18. Method for determining a component in a fluid sample, which comprises using a sensor device as claimed in claim 1.

19. Method as claimed in claim 18 wherein the component to be determined is hydrogen peroxide which is determined either directly by being present as such or indirectly by being generated from another component or analyte.

20. Method as claimed in claim 18 wherein the component to be determined is oxalate and which is determined either directly as such or as another compound generated therefrom.

21. Method as claimed in claim 20 wherein the means for detecting the oxalate which has passed through the un-plasticized polyvinyl chloride membrane is either an enzymic one or one which detects and measures the oxalate directly by electrolytic action.

22. Method as claimed in claim 18, employed for the study of biological fluids.

23. A multiple-layer membrane product, comprising at least one membrane layer composed of un-plasticized polyvinyl chloride which is selectively permeable to hydrogen peroxide, oxalate and oxalic acid and impermeable to paracetamol and an enzyme for converting one analyte component into another which is more readily determined at a detector means.

24. A membrane according to claim 23 wherein the enzyme is an oxidase.

* * * * *